(12) United States Patent
Falk-Jordan et al.

(10) Patent No.: US 7,480,053 B2
(45) Date of Patent: Jan. 20, 2009

(54) POSITION DETECTION BASED ON TWO-DIRECTIONAL CORRELATION

(75) Inventors: Stefan Falk-Jordan, Karlsruhe (DE); Bernd Nawracala, Karlsruhe (DE); Hans-Peter Zimmermann, Waldbronn (DE)

(73) Assignee: Agilent Technologies, Inc., Santa Clara, CA (US)

( * ) Notice: Subject to any disclaimer, the term of this patent is extended or adjusted under 35 U.S.C. 154(b) by 196 days.

(21) Appl. No.: 11/506,528

(22) Filed: Aug. 18, 2006

(65) Prior Publication Data

US 2007/0097357 A1    May 3, 2007

(30) Foreign Application Priority Data

Nov. 2, 2005    (EP)    ................................ 05110249.9

(51) Int. Cl.
*G01B 11/26* (2006.01)
*G01C 1/00* (2006.01)
*G01N 21/86* (2006.01)
*G01N 33/53* (2006.01)

(52) U.S. Cl. ........................ 356/444; 356/246; 356/244; 250/559.29; 435/7.2

(58) Field of Classification Search ......... 356/614–625, 356/246, 5.09, 244, 432–444; 250/559.29, 250/559.4, 559.22, 559.24, 559.26; 702/142, 702/159, 158; 435/7.2, 288.4; 422/101, 422/102, 104

See application file for complete search history.

(56) References Cited

U.S. PATENT DOCUMENTS

| | | | | |
|---|---|---|---|---|
| 6,018,388 | A * | 1/2000 | Nawracala et al. | 356/246 |
| 6,353,475 | B1 * | 3/2002 | Jensen et al. | 356/244 |
| 6,468,763 | B1 * | 10/2002 | Farinas | 435/29 |
| 6,481,648 | B1 * | 11/2002 | Zimmermann | 239/690 |
| 6,801,875 | B1 * | 10/2004 | Wolk et al. | 702/158 |
| 6,942,837 | B2 * | 9/2005 | Frye et al. | 422/104 |
| 7,023,007 | B2 * | 4/2006 | Gallagher | 250/559.29 |
| 7,312,085 | B2 * | 12/2007 | Chou et al. | 436/43 |
| 2002/0015147 | A1 | 2/2002 | Maher et al. | |
| 2002/0143437 | A1 * | 10/2002 | Handique et al. | 700/266 |
| 2003/0127610 | A1 | 7/2003 | Gallagher | |

OTHER PUBLICATIONS

European Search Report dated, Jul. 7, 2006.

* cited by examiner

*Primary Examiner*—Sang Nguyen
(74) *Attorney, Agent, or Firm*—Marc Bobys

(57) ABSTRACT

A method of determining position information, the method having detecting—along a first direction—a value of a geometry parameter related to a structure formed on and/or in a substrate, and determining—with regard to a second direction—a value of a position parameter based on the detected value of the geometry parameter and a predetermined relationship between the geometry parameter and the position parameter.

9 Claims, 4 Drawing Sheets

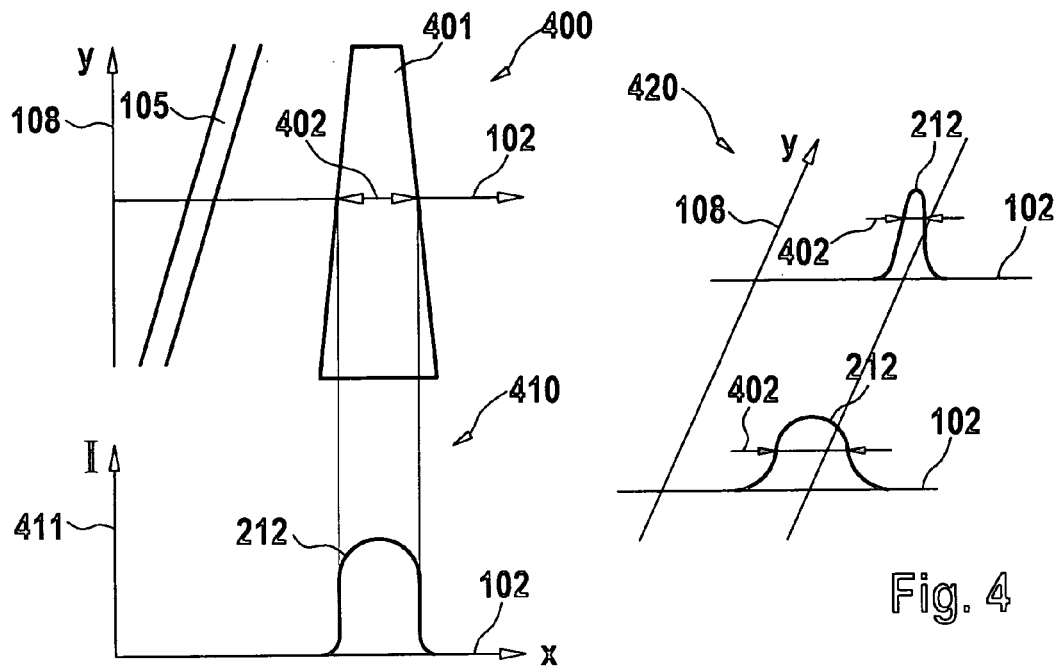
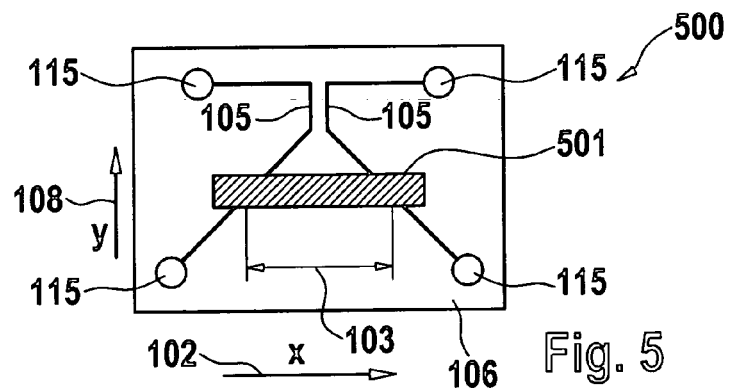
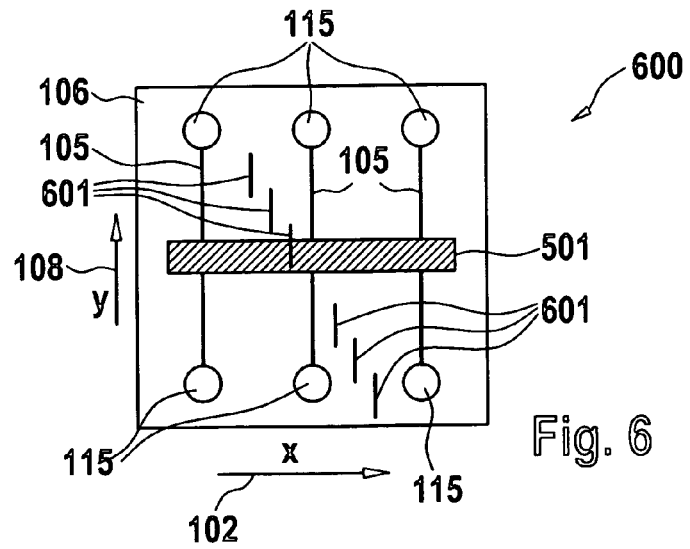

POSITION DETECTION BASED ON TWO-DIRECTIONAL CORRELATION

BACKGROUND

The present invention relates to position detection.

In a microfluidic device, channels may be formed in a substrate, and materials like gel, liquids or sample material may be transported through the channels. This can be accomplished, in the field of gel electrophoresis, by applying electric fields along the channels so that charged particles may be moved along the channels under the influence of an electric force.

In a fluid separation system of such a microfluidic device, different components which are separated, using electric fields or the like, may be detected optically. For this purpose, a light beam may be emitted onto a channel, so that molecules moving along the channel can be detected, for instance due to their fluorescence properties.

For microfluidic applications, particular requirements might have to be considered when determining and adjusting the detection position of an instrument. This holds for the transverse directions (like horizontal and vertical position relative to a chip structure, for instance a channel) and also for a longitudinal direction. Examples for such chip structures are applications related to flow-injection and component separation. It might be important or necessary, for a sufficient detection sensitivity, to be in conformity with accurate time and/or spatial distances relative to reference positions.

It may happen that the time dependence of a concentration ratio or an equilibrium state of used chemical agents, in the context of transport procedures using channels, correlates with a position on the chip or along a channel. For instance, for fluorescence detection with sample derivatization, it has to be considered during a measurement using a fluorescence label that the reaction time may be limited by effects like diffusion.

In the light of the small dimensions of microfluidic devices, even moderate requirements concerning relative positioning accuracy can correspond to very small absolute tolerances which, in many cases, are difficult to obtain or are obtainable only with high effort by sophisticated manufacturing procedures.

In many cases, measurement devices are used which enable to position a detector using an adjustment device before the measurement. However, such an adjustment may be complicated and time-consuming.

SUMMARY

It is an object of the invention to provide a system of determining position information on a substrate with reasonable effort. The object is solved by the independent claims. Further embodiments are shown by the dependent claims.

According to an exemplary embodiment of the present invention, a method of determining position information (for instance as a basis for adjusting a position of a microfluidic device) is provided, the method comprising detecting—along a first direction (for instance along an x-axis of a microfluidic device)—a value of a geometry parameter (for instance containing absolute or relative geometric information) related to a structure (for instance comprising a channel and/or a bar) formed on and/or in (for instance deposited on or integrated in) a substrate (for instance a glass chip), and determining—with regard to a second direction (for instance along an y-axis of a microfluidic device which is aligned perpendicular with respect to the x-axis)—a value of a position parameter (for instance the value of the y-position) based on the detected value of the geometry parameter and a predetermined relationship (for instance a unique or an unambiguous correlation) between the geometry parameter and the position parameter.

According to another exemplary embodiment, an apparatus for determining position information is provided, the apparatus comprising a detecting unit (for instance an optical detection system) adapted for detecting—along a first direction—a value of a geometry parameter related to a structure formed on and/or in a substrate, and a determining unit (for instance a microprocessor) adapted for determining—with regard to a second direction—a value of a position parameter based on the detected value of the geometry parameter and a predetermined relationship between the geometry parameter and the position parameter.

According to still another exemplary embodiment, a fluid separation system (for instance a gel electrophoresis device) for separating compounds of a fluid flowing in a substrate is provided, the fluid separation system comprising a separation unit adapted for separating compounds of the fluid, an identification unit adapted to identify the separated compounds of the fluid, and an apparatus having the above mentioned features for determining position information of the substrate with regard to the identification unit so as to allow for a positional adjustment of the substrate with regard to the identification unit.

According to yet another exemplary embodiment, a product is provided comprising a substrate and a structure formed on and/or in the substrate, wherein a value of a geometry parameter related to the structure is detectable along a first direction, and wherein a value of a position parameter is determinable with regard to a second direction based on the detected value of the geometry parameter and a predetermined relationship between the geometry parameter and the position parameter.

Embodiments can be partly or entirely embodied or supported by one or more suitable software programs, which can be stored on or otherwise provided by any kind of data carrier, and which might be executed in or by any suitable data processing unit. Software programs or routines can be applied for controlling or carrying out a method of determining position information having the above mentioned features. The method of determining position information according to an exemplary embodiment can be realized by a computer program, i.e. by software, or by using one or more special electronic optimization circuits, i.e. in hardware, or in hybrid form, i.e. using software components and hardware components.

According to an exemplary embodiment, a simple and efficient way of determining a correct position in at least two dimensions is provided. In such a two-dimensional substrate configuration, in which a surface of a substrate is defined by two dimensions, namely a first direction and a second direction, a scan, for instance with a light beam, may be carried out along the first direction in order to detect geometric information related to a structure (which may be formed of one or more sub-structures, like microfluidic channels, auxiliary structures, etc.). Based on such a geometry parameter, for instance a distance between two sub-structures measured at a particular position of the second direction by scanning along the first direction, information concerning the present position along the second direction may be derived. When a correlation between the measured geometry parameter on the one hand and a corresponding or assigned position along the second direction on the other hand is pre-known (for instance has been measured beforehand or is known from a manufacturing process) then it is possible to derive the current second position based on this pre-known correlation and based on the measured value of the geometry parameter.

Adjusting a relative position between different components of a measurement device based on the evaluated current position may allow to obtain a very good long time stability, if desired regulation or repeated adjustment of the position may further improve the quality of alignment.

By taking this measure, it may be possible to detect and, if desired, re-adjust the current position on a two-dimensional substrate based on a one-dimensional scan. With this in mind, it may be possible to accurately adjust a detection position in a microfluidic device, for instance to ensure that a laser beam for optically detecting a separated component of a fluid of a fluid separation device is correctly located with respect to a microfluidic channel through which the components to be separated may be transported (for instance using gel electrophoresis).

An adjustment according to the descried embodiments may be simple and fast.

Thus, using a pre-known mapping rule between the detected geometry parameter and a corresponding position along the second direction and by measuring the current value of the geometry parameter, a well-defined assignment between a position along the second direction and a value of the geometry parameter may allow to accurately determine the position along the second direction.

Thus, according to an exemplary embodiment, chip detection with xy-information may be enabled. An adjustment along a first direction, which may be denoted as an x-direction, may be easy due to properties of the channel structure. In case that the channel is aligned along the y-direction, and when a scan is performed along the x-direction, reflection or dye properties of the channel which differ from the environment may enable to accurately determine whether the light beam is positioned correctly with respect to the x-direction. However, when an accurate y-direction of the channel through which fluid is flowing has to be determined, the reflection or dye properties of the channel which differ from the environment may be insufficient for estimating whether a correct y-position has been adjusted. In other words, essentially no variation of the detector signal in the y-direction occurs in case of reference conditions (calibration). However, according to an exemplary embodiment, a scenario may be properly handed in which a sample shows different behaviour in the Y-direction.

The structure (which may comprise the channel and/or auxiliary sub-structures which are particularly formed for this purpose) may allow to map the geometry into a detector signal. In other words, when the geometrical properties of the structure vary along the second direction, and when such a varying or spatially dependent parameter is being measured at a particular y-direction, then a pre-known correlation between y-direction and the value of the geometrical property can be used to determine at which position the light beam or other reference mark is currently positioned.

The estimation of the correct transversal measuring position (for instance a direction perpendicular to the extension of the channel) may be, as described above, quite easy in many cases due to local varying properties. This results from the fact that chip structure elements like channels may allow for a proper orientation, due to their differing properties with respect to the environment. However, the longitudinal positioning (for instance a direction parallel to the extension of the channel) is more problematic in a conventional scenario, particularly when in this direction homogeneous conditions are present. According to an exemplary embodiment, such problems may be overcome by scanning the substrate along a direction perpendicular to the extension of the channel and using a known correlation between a parameter detected during the scan and a position along the direction parallel to the extension of the channel.

According to an exemplary embodiment, the geometry of the channel system is aligned or arranged in such a manner that, using the geometrical position of different structures forming such a channel system with respect to one another, may provide information concerning the accurate detection position, at which the measurement will be performed.

Exemplary fields of use are all application chips, particularly all application chips in which scans over the chip are performed, and of which a pattern may be obtained based on which the geometrical properties may be determined. Particularly, a method of determining position information according to an exemplary embodiment may be implemented in all kind of test chips (for instance instrument tests, application simulations, etc.) or can be applied to chips in which locally distributed structures are to be scanned.

In a microfluidic application including channels, a detection spot (for instance an optical light beam) may be used to transfer components to be separated into an excited optical state which, for instance using fluorescence, then relaxes to a ground state under emission of a photon. Such a photon may then be measured. Alternatively, absorption measurements can be carried out in such a scenario in which light transmitted through the fluid and the substrate is analyzed. However, in many cases, a plurality of different channel structures may be provided in parallel to one another so that it is possible to move the spot between the channels and perform a proper adjustment along a first direction, that is a position along a first direction of a substrate along which the measurement shall be performed. This position may be a central part of a channel. However, it may happen in the case of special samples that also a second direction, which may be perpendicular to the first direction, may be of interest concerning a proper positional adjustment, since the properties of an analyt to be separated may vary also along this second direction, or since a proper adjustment along the y-direction may be necessary for a proper analyt analysis.

According to an exemplary embodiment, the channel structure maps the x-direction to the y-direction. In a first procedure, an optimized x-direction may be adjusted. Next, a desired y-position may be adjusted based on a detected geometrical property with regard to the x-direction and based on a correlation between a value of this geometry parameter and the position along the y-direction.

Thus, known geometrical conditions along the y-direction may be used to determine the current value of the y-direction based on a measurement of this condition along the x-direction.

It is possible to use, as the geometry parameter, a relative property of different channels to one another, for instance a distance between the two channels which varies along the second direction. However, it is also possible to use the properties of a single channel, for instance if the width of such a channel or auxiliary structure varies along the second direction or if a channel has varying optical properties along the second direction.

For instance, a channel with an inhomogeneous thickness along the second direction may be used. In order to avoid a distortion of the sample transport or separation resulting from the inhomogeneous thickness of the channel, other properties of the channel, for instance the depth of the channels may be adjusted to compensate for those effects. By taking this measure, the cross-sectional area of the channel may be kept essentially constant although the channel width varies along its extension.

According to an exemplary embodiment, an information along a second direction is sampled in such a manner along a first direction that the information concerning the second direction is derivable.

For the detection, proteins as an example for a fraction or component of an analyt to be investigated may be coupled to a fluorescence label so as to enable an optical detection. In such a scenario, an accurate positional adjustment of the light beam can be important, since the different fractions of the analyt may be detectable only at particular positions.

Examples for components (or sub-structures) of the structure are:

channels used during microfluidic applications dents, grooves or notches provided in a substrate or chip etching structures (dents or elevations) which are formed by patterning a photoresist, for instance simultaneously with forming channels. Examples for such etching structures are remaining portions of photoresist or trenches etched between portions of the photoresist.

color markings provided on the surface of the substrate doped portions in or on the substrate, for instance doped portions of a glass chip (for instance ruby)

metal filaments provided on or in the substrate (for instance silver filaments)

mirror portions for a reflection measurement

For providing an optical detection spot, a laser may be used (for instance a laser diode or a NdYAG laser).

As alternatives to an optical detection of a position or of a geometry parameter, electrical detection methods are possible (for instance measuring a value of an ohmic resistance), radioactive markers may be implemented, or a mechanical scan for sampling a surface topography may be possible with a (microscopic) tip.

Exemplary fields of applications are gel electrophoresis, fluorescence measurement, electrophoresis in general, separation methods, liquid chromatography (column arrangements), any microfluidic applications, particularly pressure induced transport of particles. Furthermore, the system according to an embodiment may be used in the context of a lab-on-chip.

The manufacture of the structure (or components thereof) may be performed using mask and lithography processes, so that a high accuracy of some nanometers and less may be obtained.

The system according to an exemplary embodiment may also be implemented in semiconductor technology, for instance for adjustment of lithography, mask positioning and multilayer formation devices.

Typical dimensions of components of the structure are 1 mm to 50 mm in length, 20 µm to 200 µm in width, 8 µm to 30 µm in depth.

When components of the structure have a varying width along the second direction, the value of the width along the first direction may be scanned in order to collect information concerning the second direction.

As materials for the substrate, glass, plastics, ceramics, semiconductor and metal can be used. Ceramics materials may be suitable because this may allow to form recesses as components of the structure using a laser. Due to the high stability of a metallic material, such a substrate may be suitable for pressure induced investigations.

The system according to an exemplary embodiment may not only be implemented in two dimensions, but it is also possible to adjust a position along a third dimension. For instance, a scan along the third direction, which may be denoted as the z-direction may be performed. In such a scenario, a first scan may be performed along the x-direction. The detection and calculation of the position along the y-direction which forms together with the x-direction the plane of the substrate may be performed as described herein. Additionally, an optional scan along the z-direction, i.e. the depth, is possible, for instance by tilting or turning the substrate.

According to an exemplary embodiment, the system may be used in the context of an integrated circuit formed in a semiconductor substrate, for instance in a silicon chip. Also in such a scenario, it is possible to provide structures and to determine geometrical information concerning the structures in an integrated circuit (for instance the distance between portions of a patterned layer, or trenches formed in the semiconductor substrate) by inspecting the spatial relation between structures or structural components. For ensuring a proper alignment between a processing unit and an integrated semiconductor circuit, an accurate knowledge of the geometrical properties of the integrated circuit components can be required.

Next, further exemplary embodiments will be described.

In the following, exemplary embodiments of the method of determining position information will be described. However, these embodiments also apply for the apparatus for determining position information, for the fluid separation system and for the product.

The detecting may comprise scanning the substrate along the first direction. Such a scanning or sampling may be performed by moving a detection unit relative with respect to the substrate. For this purpose, the detection unit may be moved and the substrate may be fixed, or the detection unit may be spatially fixed and the substrate may be moved.

The scanning may particularly comprise moving a beam of electromagnetic radiation along the first direction and detecting, in response to the beam, at least one of a signal reflected at the substrate and a signal transmitted through the substrate. The wavelength region of the electromagnetic radiation may be, for instance, optical light, infrared radiation, ultraviolet radiation, X-rays, y-rays, or the like.

The scanning may comprise moving a laser beam along a first direction and detecting, in response to the laser beam, at least one of a signal reflected at the substrate and a signal transmitted through the substrate. Thus, it is possible to perform a reflection measurement or a transmission measurement. Also a fluorescence measurement is possible. The laser may be a laser diode or a NdYAG laser, for instance.

The geometry parameter may be a position (absolute or relative to any desired reference point, for instance to another sub-structure or to an edge of the substrate) of the structure along the first direction. In case that there is a clear and unique correlation between the position of the structure along the first direction on the one hand and a corresponding spatial position along the second direction on the other hand, this information may be used to determine the current position along the second direction based on this known correlation and based on the information derived from the scan.

The geometry parameter may also be a detection signal intensity related to the structure along the first direction. In case that the detection signal intensity depends on the position along the second direction, for instance since the structure has varying reflection, transmission or fluorescence properties along the second direction (for instance a spatial dependence of a pigment concentration along the second direction), then this information can be used to derive, from a measured value of the signal intensity at a particular position along the first direction, the corresponding position along the second direction.

However, the geometry parameter may also be a width of the structure along the first direction. When the structure, for instance an auxiliary structure or a channel, has a varying width along the second direction, then the detection of the particular value of the width at particular position along the first direction may provide the necessary information to derive the position along the second direction.

The predetermined relationship between the geometry parameter and the position parameter may be a predetermined mathematical function defining the relationship between the geometry parameter and the position parameter. Calculating the measured geometry parameter in such a function may allow, with reasonable computational burden, to unambiguously derive the value of the current position along the second direction.

The determining may also be based on counting the number of sub-structures of the structure traversed during the scanning. Thus, some kind of digital sampling the first direction may be performed, so that a number of strips or the like are counted which are traversed during the scanning, and the number of strips may be taken as a measure for the current position along the second direction. For instance, the density of strips may vary along the second direction.

The method may further comprise forming the structure using a lithography process and/or a laser treatment. By a lithography process using a photoresist layer to be patterned, a bar like structure may be generated. Using a laser treatment, recesses may be formed which may be used as the structure or as sub-structures of this structure.

In the following, exemplary embodiments of the fluid separation system will be described. However, these embodiments also apply for the method of determining position information, for the apparatus for determining position information and for the product.

For an electrophoresis application, channels may be etched in a first glass chip or a glass wafer with a width of for instance 30 μm to 200 μm, and with a depth of, for instance, 8 μm to 25 μm. Then, a second glass chip may be provided with through holes as contact channels. The second substrate may be bonded to the first substrate so that the through holes in the second substrate match with the channels in the first substrate which allows to introduce material in the channels of the first substrate by inserting this material in the through holes being in fluid communication with the channels. The channels and/or the through holes may also serve as sub-structures of the structure and thus as a source of position information.

For a gel electrophoresis experiment, gel material and an analyt may be introduced through the through holes into the channels. Such an experiment can require an accurate knowledge of the geometrical parameters characterizing the channels and may require a proper adjustment of a detection unit with respect to these channels.

The channels and the substrate may be manufactured by illuminating the substrate covered with a photoresist by selectively removing the illuminated portions (or the non-illuminated portions) of the photoresist layer on the substrate by etching, and by removing material of uncovered regions of the glass chip using a suitable etching process (for instance chemical etching, wet etching, dry etching, plasma etching, laser etching or the like). Thus, a combination of optical lithography and etching may be used for forming the structure (or the sub-structures of the structure).

The substrate to be processed or investigated according to an exemplary embodiment may be a glass substrate like a round or quadratic glass wafer with linear dimensions of, for instance, 4 inch or 8 inch. Such a wafer may be divided into a plurality of chips having, for instance, a rectangular shape with a linear dimension in the range between, for instance, 17.4 mm and 57 mm.

In the fluid separation system, the fluid may be insertable in at least one of a plurality of sub-structures of the structure formed on and/or in the substrate. In other words, the structure does not necessarily have to be a single component, but may also comprise a plurality of different sub-components or sub-structures, like bars, recesses, channels, or the like. The fluid may be inserted in such channels so that these channels may also be denoted as functional channels or functional structures. Namely, these structures may be used for both, containing fluid for the measurement and serving as a geometrical marker as a source of information concerning the position on the chip.

The identification unit may be an optical identification unit to optically identify the separated compounds of the fluid. Such an optical identification unit may comprise a light source adapted to generate a light beam which is directed to the substrate, and a detection unit (for instance a photodiode or the like) which is capable of detecting light reflected by the substrate or transmitted through the substrate. In the context of such an optical identification system, particles to be detected may be provided with a fluorescence label so that the fluorescence radiation may be used to detect the particles.

Alternatively, the identification unit may be an electrical identification unit to electrically identify the separated components of the fluid. For instance, a value of an ohmic resistance or a conductivity may be measured, for instance when a fraction of the fluid passing through the channels has a characteristic conductivity which is distinguished from the conductivity of other components.

The identification unit may also be a radiation identification unit to detect radioactive radiation emitted by the separated components of the fluid. In such a scenario, a radioactivity detector may be used to detect radioactive radiation emitted by the fraction of the analyt to be examined. For instance, radioactive labels may be attached to the components of the analyte.

However, the identification unit may also be a mechanical identification unit to identify the separated components of the fluid by a mechanical scan. For instance, a micro-tip may be used to mechanically scan a chip and to detect particles based on such mechanical information.

In the following, exemplary embodiments of the product will be described. However, these embodiments also apply for the method of determining position information, for the apparatus for determining position information and for the fluid separation system.

The first direction may be different from the second direction, particularly may be essentially perpendicular to the second direction. In other words, the first direction and the second direction may define a plane together, which may be a surface plane of the substrate.

The structure may comprise a first sub-structure and a second sub-structure, and the geometry parameter may be a distance between the first sub-structure and the second sub-structure. In such a scenario, this distance may vary along the extension of the second direction so that the measurement of the distance may be used as an information to derive the position along the second direction.

The structure may be a recess, a color marking, a bar on the substrate, a doped portion of the substrate, a mirror portion of the substrate, or a metallic portion of the substrate. More generally, the structure may be particularly any portion of the substrate which differs concerning a measurable material property from the surrounding material.

The substrate may comprise one of the group consisting of a glass, a semiconductor, a plastics, a ceramics and a metal. When using a semiconductor substrate, this can be made from silicon, germanium, or a group III-group V semiconductor, like gallium arsenide.

The structure may be a functional structure adapted to provide a function of the product. In other words, the structure may then provide two functions at the same time, namely the actual function of the product (for instance serving as a channel for a microfluidic application) on the one hand and serving as a source of information for estimating a position along the second direction.

The functional structure may be a channel of a fluid separation device, wherein the fluid separation device may be one of the group consisting of a gel electrophoresis device, a pressure induced fluid separation device, and a liquid chromatography device. However, the product is not restricted to one of these applications.

Particularly, the product may be employed in a measurement of at least one physical, chemical, or biological parameter of an analyt under examination. Examples for physical parameters are temperature, pressure, volume or the like. Examples for chemical parameters are a concentration, a pH-value, or the like. Examples for biological parameters are presence or absence of proteins or genes in a solution, biological activity in a sample, or the like.

Furthermore, the product may be used together with a sensor device, a test device for testing a device on a test or a substance, a device for chemical, biological and/or pharmaceutical analysis, a fluid separation system adapted for separating components of a fluid, a capillary electrophoresis device, a liquid chromatography device, a gas chromatography device, an electric measurement device, and a mass spectroscopy device. Thus, exemplary application fields of the product may be gas chromatography, mass spectroscopy, UV spectroscopy, optical spectroscopy, IR spectroscopy, liquid chromatography, and capillary electrophoresis bioanalysis. More generally, the product may be integrated in an analysis device for chemical, biological and/or pharmaceutical analysis. Such an analysis system may be a fluid separation device, a liquid chromatography device, an electrophoresis system, or the like. In a realization of the product in the context of a device for chemical, biological and/or pharmaceutical analysis, functions like (protein) purification, electrophoresis investigations of solutions, fluid separation, or chromatography investigations may be performed.

However, the structure of the product may also be an auxiliary structure which is provided exclusively for determining position information of a substrate. Thus, the structure may serve to provide the geometrical information.

Particularly, the substrate may be a microstructure substrate (which may comprise structures in the dimension of micrometers).

Furthermore, the product may be adapted as a fluidic product, particularly as a microfluidic product. Such a fluidic product may be a product having channels into which a fluid or a gel may be introduced. "Microfluidics" may particularly relate to the science of designing, manufacturing and formulating devices and processes that deal with volumes of fluid in the order of microlitres or in channels having dimensions of micrometers. Such devices themselves may particularly have dimensions ranging from centimeters to millimeters or micrometers.

However, the product may also be adapted as a nanofluidic device having dimensions in the order of nanometers or less, or volumes of nanolitres or even picolitres.

The product may be one of the group consisting of a fluid separation product, a gel electrophoresis product, and a liquid chromatography product, that is to say a product which is used in the respective technology.

The length of the structure may be in the range between essentially 1 mm and essentially 50 mm, more particularly in the range between essentially 10 mm and essentially 20 mm. A width of the structure may be between essentially 20 μm and essentially 200 μm; more particularly in the range between essentially 50 μm and essentially 100 μm. Furthermore, a depth of the structure may be in the range between essentially 8 μm and essentially 30 μm, more particularly in the range between essentially 15 μm and essentially 25 μm.

BRIEF DESCRIPTION OF THE DRAWINGS

Other objects and many of the attendant advantages of embodiments of the present invention will be readily appreciated and become better understood by reference to the following more detailed description of embodiments in connection with the accompanied drawings. Features that are substantially or functionally equal or similar will be referred to by the same reference signs.

FIG. 2 to FIG. 4 show arrangements based on which a measuring principle according to exemplary embodiments is explained.

FIG. 5 to FIG. 9 show products according to exemplary embodiments.

Figure 1:
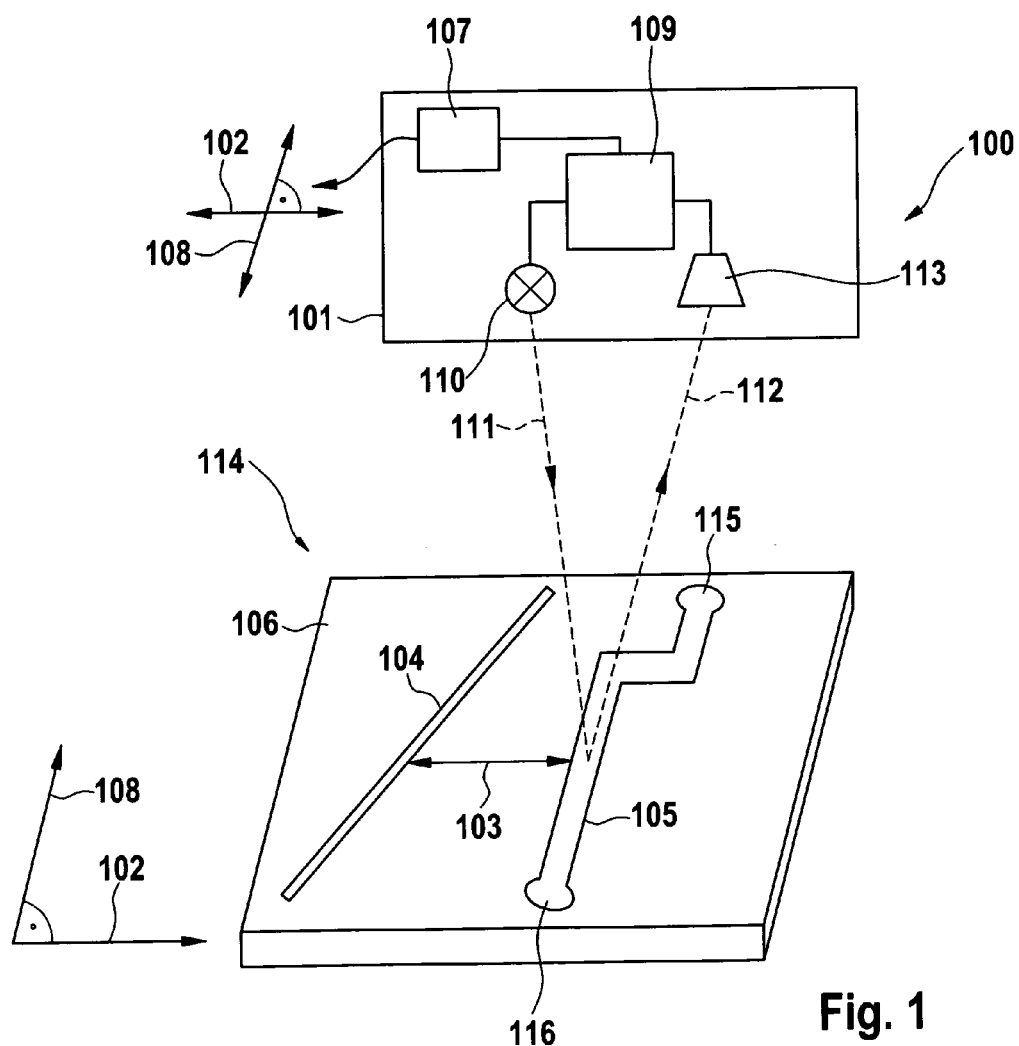
FIG. 1 shows an apparatus for determining position information according to an exemplary embodiment.

The illustration in the drawing is schematically.

DETAILED DESCRIPTION OF THE DISCLOSED EMBODIMENTS

In the following, referring to FIG. 1, an apparatus 100 for determining position information according to an exemplary embodiment will be described.

The apparatus 100 comprises a detecting unit 101 which is adapted for detecting—along a first direction 102—a value of the distance 103 between an auxiliary structure 104 and a channel 105, both formed as recesses in a glass substrate 106.

Furthermore, the apparatus 100 comprises a determining unit 107 for determining—with regard to a second direction 108—the relative position of the substrate 106 with respect to the detecting unit 101 along the second direction 108 based on the detected distance 103 and based on a predetermined mathematical or numeral relationship between the distance 103 and the position along the second direction 108. As can be taken from FIG. 1, the first direction 102 is oriented orthogonal to the second direction 108, wherein the directions 102, 108 form the surface plane of the substrate 106.

The detection unit 101 comprises a control unit 109 which controls light emission of a laser diode 110 adapted to emit a light beam 111 onto a surface of the substrate 106. After reflection of the light beam 111 at the channel 105 of the substrate 106 according to the configuration shown in FIG. 1, the reflected light beam 112 is directed to a detector 113 (for example a photodiode) of the detection unit 101. The corresponding detection signal is provided to the control unit 109. The control unit 109 may forward the detection signal of the detector 113 to the determining unit 107 which then determines the distance 103. Based on a look up table (pre-stored in a memory device) correlating a measured value of the distance 103 to a position along the second direction 108, the position along the second direction 108 may be estimated. The position along the first direction 102 may be estimated easily based on the optical properties varying along the first direction 102, i.e. being different at the positions of the channel 105 and of the recess 104.

For detecting the distance 103, the detection unit 101 may be moved along the first direction 102 so as to scan a region between the auxiliary recess 104 and the channel 105 at a particular position along the second direction 108.

For a proper operation of the system 100, a corresponding geometrical relationship between the various components of FIG. 1 has to be ensured and may be regulated, if desired.

Since the auxiliary structure 104 and the channel 105 have optical characteristics and thus a reflectance which differs from other portions of the substrate 106, corresponding peaks (or spectral dips) may be detected when the light source 110 emits the electromagnetic radiation beam 111 onto one of the structures 104, 105.

Based on evaluated information about the two-dimensional position of the substrate 106 with respect to the detection unit 101, it can be judged whether the relative positioning is acceptable or should be corrected by moving the substrate 106 with respect to the detection unit 101. In an acceptable position, it should be possible that light 111 of the laser 110 is emitted into a central part of the channel 105 and that the reflected light propagates towards the detector 113. The positional adjustment of the laser 110, the channel 105 and the detector 113 may be performed in advance of a fluid separation experiment which may also be carried out with the configuration of FIG. 1. Thus, the apparatus 100 may be also used as a fluid separation system, namely may be integrated therein.

The substrate 106 including the structures 104, 105 is a microfluidic product 114. The channel 105 may be used for a gel electrophoresis investigation and may be filled with gel and/or with an analyt to be investigated. Thus, along an extension of the channel 105, an electric field may be applied and, under the influence of the magnetic field force, sample provided in sample containers 115 may be moved along the extension of the channel 105. When components of the analyt are labeled with fluorescence molecules, then the fluorescence light emitted by such components of the analyt may be detected by the detector 113 after having excited the fluorescence molecules by photons of the light source 110. By taking this measure, the presence and the concentration of the molecule fractions of the analyt moved along the channel 105 may be analyzed.

However, for an accurate excitation of such molecules, it has to be ensured that the alignment between the detection unit 101 and the substrate 106 is such that the emitted light beam 111 is impinged on a central portion of the channel 105. For this purpose, it can be necessary to have position information concerning the substrate 106 with respect to the detection unit 101, and to re-adjust the locations of the various components, if necessary.

In the following, referring to FIG. 2, an arrangement will be described based on which the measuring principle according to an exemplary embodiment of the invention will be described.

Figure 2:
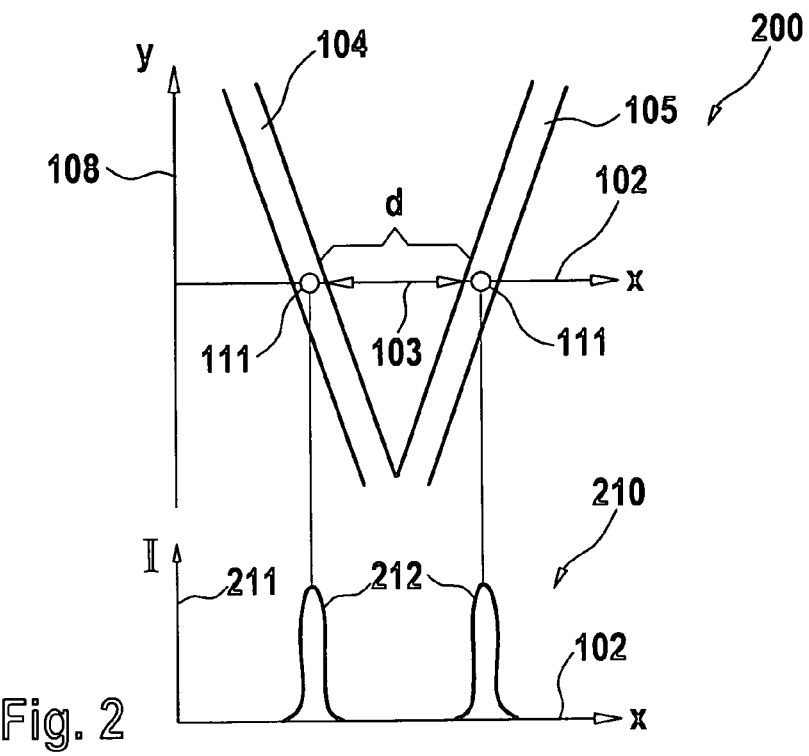

FIG. 2 shows a diagram 200 having an abscissa which corresponds to the first direction 102. An ordinate of the diagram 200 corresponds to the second direction 108. The position of the light beam 111 impinging on the auxiliary structure 104 and on the channel 105 is shown in FIG. 2 as well.

FIG. 2 further shows a diagram 210 having an abscissa along which the first direction 102 is plotted. Along an ordinate 211 of the diagram 210, the intensity of a signal as measured by the detector 113 is plotted. As can be taken from the second diagram 210, when the light beam 111 is emitted onto one of the structures 104, 105, the signal intensity 211 differs from a signal intensity 211 which is detected during the scan along the first direction 102 between the structures 104, 105, so that the distance between the peaks 212 of the intensity diagram 211 corresponds to the distance 103 to be measured. Since the look up table of the determining unit 107 includes a correlation between a particular distance 103 and a corresponding position along the second axis 108, it is possible to determine the distance 103.

Figure 3:
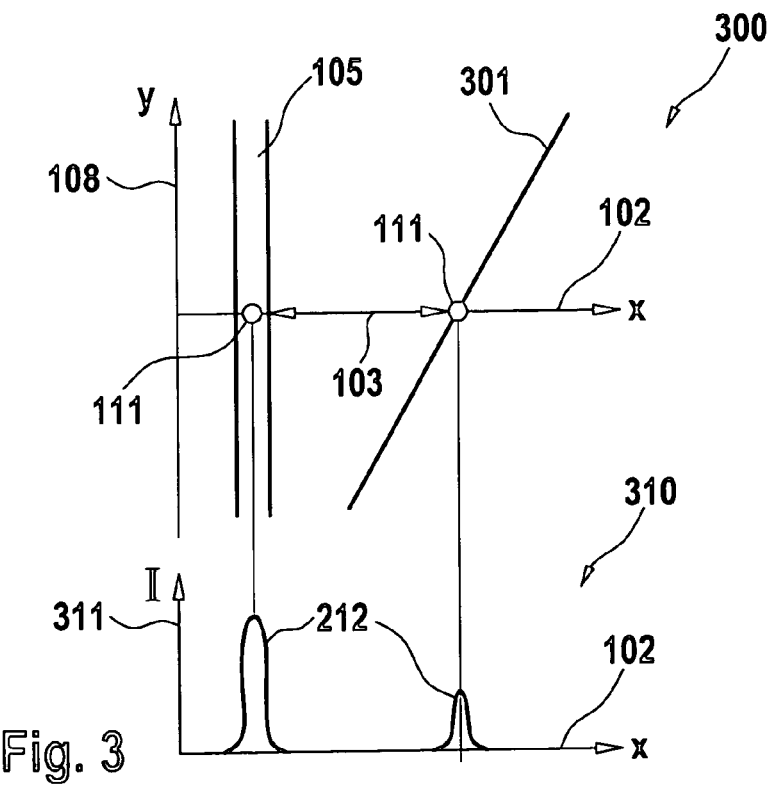

FIG. 3 shows an alternative configuration.

In the scenario of FIG. 3, the structures formed on the substrate 106 are a channel 105 and a doped portion 301 of the substrate.

FIG. 3 shows a diagram 300 having an abscissa which corresponds to the first direction 102. An ordinate of the diagram 300 corresponds to the second direction 108. The position of the light beam 111 impinging on the doped portion 301 and on the channel 105 is shown in FIG. 3 as well.

Since the doped portion 301 has optical properties which differ from the optical properties of the other portions of the substrate 106, a peak 212 can be detected in the intensity diagram 310 along an ordinate 311. Thus, according to the scenario of FIG. 3, the scan again allows to determine the distance 103, thus allowing to calculate the position along the second axis 108.

In the following, referring to FIG. 4, another configuration will be described.

FIG. 4 shows a diagram 400 having an abscissa which corresponds to the first direction 102. An ordinate of the diagram 400 corresponds to the second direction 108.

The diagram 400 shows the channel 105 and an auxiliary structure 401 being a metallic portion with a varying width along the second direction 108. In the scenario shown in FIG. 4, the geometrical information to be detected is a value of a width 402 of the auxiliary structure 401 which can be detected by scanning a portion surrounding the auxiliary structure 104, as shown in a diagram 410. In the diagram 410, an intensity 411 is plotted. The width of a peak 212 thus detected corresponds to a width of the auxiliary structure 401 at the particular position along the second direction 108.

As can be taken from a further diagram 420 of FIG. 4, due to the value of the width 402 varying along the second direction 108, the width of the detection peak 212 essentially depends on the position along the second direction 108. Thus, considering the known correlation between the width 402 and the position along the second direction 108, and by detecting the width 402 of the peak 212, it is possible to derive information about the corresponding position with respect to the second direction 108.

In the following, referring to FIG. 5, a product 500 according to an exemplary embodiment will be described.

The product 500 comprises two fluid channels 105 which are scanned along a first direction 102 (see scanning portion 501, that is the area passed by the light beam during the scan) so as to detect a distance 103 between the two channels 105 to receive information about the y-axis 108.

After having scanned the two channels 105 arranged in a V-shape and after subsequent distance 103 estimation, the position along the y-axis 108 can be accurately calculated based on a known relationship.

A product 600 according to an exemplary embodiment is depicted in FIG. 6.

FIG. 6 shows a substrate 106 having channels 105 and auxiliary structures 601. Using scanning the auxiliary structure 601 along a scanning portion 501, the "digital" arrangement of the auxiliary structures 601 may be used, that is to say the number and position of auxiliary structures 601 can be counted based on a detection signal pattern as a number of peaks.

Figure 7:
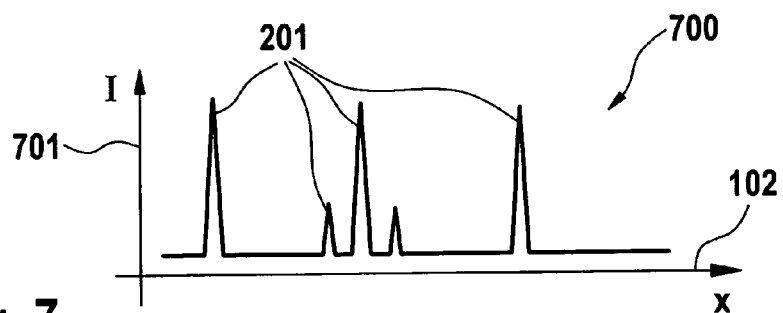

Such a pattern is shown in a diagram 700 of FIG. 7.

In the diagram 700, an intensity 701 is plotted in dependence of the position along the first direction 102.

Large peaks 201 are measured when the light beam passes the channels 105, small peaks 201 are measured when the light beam passes the auxiliary structures 601. Thus, intensity information may also used to derive position information.

In the following, referring to FIG. 8, a product 800 according to an exemplary embodiment will be described.

The product 800 comprises, in addition to the channels 105, auxiliary structures 801 which are slanted with respect to the channels 105. Thus, the configuration of FIG. 8 can be denoted as some kind of "analog" solution. The measurement of FIG. 8 essentially corresponds to the measurements of FIG. 6, 7. However, the distance values of the auxiliary structures 801 with respect to the channels 105 allow an "analog" evaluation of the scan position.

Figure 8:
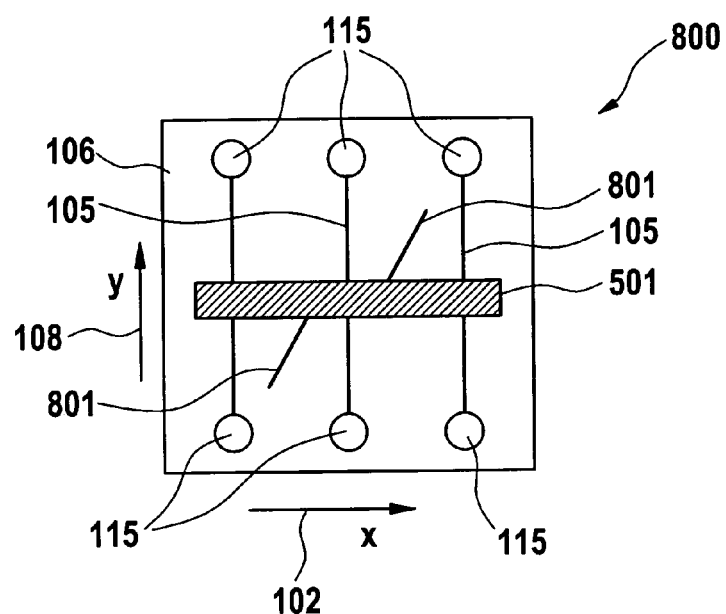
Figure 9:
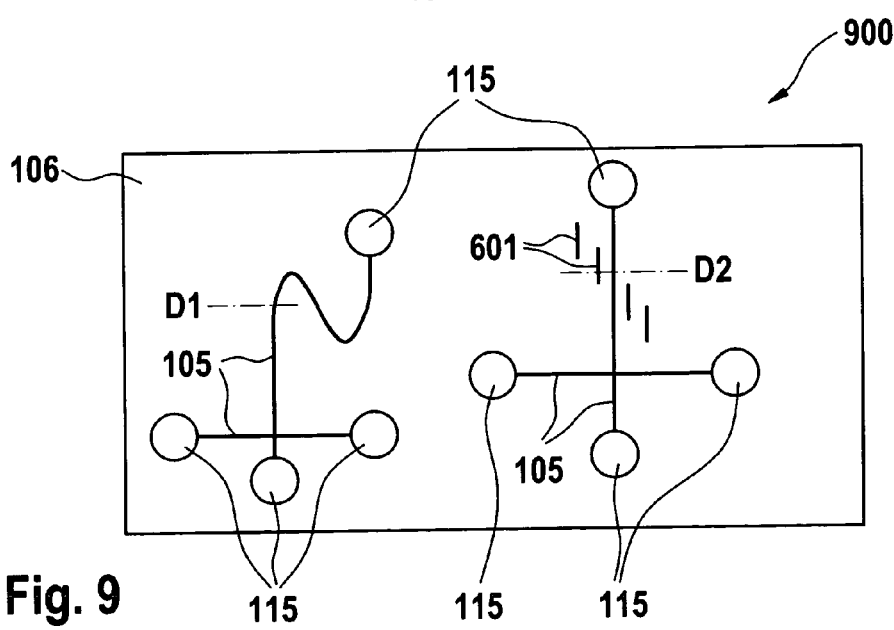

FIG. 9 shows a product 900 which includes a combination of a digital arrangement of FIG. 6 and an analog arrangement of FIG. 8. The positions D1 and D2 are the "optimum" scan points on the channels 105.

It should be noted that the term "comprising" does not exclude other elements or procedures and the "a" or "an" does not exclude a plurality. Also elements described in association with different embodiments may be combined. It should also be noted that reference signs in the claims shall not be construed as limiting the scope of the claims.

What is claimed is:

1. A method of determining the position of an apparatus with respect to a fluidic flow path on a surface of a fluidic product, the method comprising
    including at least one auxiliary structure, that is not a fluidic flow path, on the surface so that the auxiliary structure has a known spatial relationship with respect to the fluidic flow path;
    obtaining a measure involving the auxiliary structure along a first direction on the surface using the apparatus; and
    obtaining the position of the apparatus with respect to the fluidic flow path along a second direction on the surface based on the measure obtained.

2. The method of claim 1,
    wherein obtaining a measure involving the auxiliary structure along a first direction on the surface using the apparatus comprises scanning using the apparatus along the first direction to obtain the measure.

3. The method of claim 2, wherein scanning using the apparatus along the first direction to obtain the measure comprises:
    scanning one of a beam of electromagnetic radiation and a laser beam along the first direction over at least the auxiliary structure;
    detecting in response to the beam at least one of a reflected signal and a transmitted signal; and
    obtaining the measure based on the at least one of the reflected signal and the transmitted signal.

4. The method of claim 1, wherein the measure involving the auxiliary structure along a first direction on the surface comprises one of:
    a distance between the auxiliary structure and the fluidic flow path along the first direction;
    a distance along the first direction between a first auxiliary structure and a second auxiliary structure of the at least one auxiliary structure;
    a width of the auxiliary structure along the first direction; and
    a count of the number of the at least one auxiliary structure in the first direction.

5. The method of claim 1, wherein at least one of:
    the first direction is different from the second direction;
    the first direction is perpendicular to the second direction;
    the auxiliary structure is a recess in the substrate;
    the auxiliary structure is a color marking on or in the substrate;
    the auxiliary structure is a bar on the substrate;
    the auxiliary structure is a doped portion of the substrate;
    the auxiliary structure is a mirror portion on or in the substrate;
    the auxiliary structure is a metallic portion on or in the substrate;
    the fluidic product comprises one of the group consisting of glass, a semiconductor, a plastic, a ceramic, and a metal;
    the fluidic product comprises a fluid separation device, wherein the fluid separation device is one of the group consisting of a gel electrophoresis device, a pressure induced fluid separation device, and a liquid chromatography device;
    the auxiliary structure is provided exclusively for determining position information of a substrate;
    the fluidic product is configured as a microfluidic product;
    the fluidic product is configured as a nanofluidic product;
    the fluidic product is configured as a microstructure product;
    the fluidic product is configured as a nanostructure product;
    the fluidic product is one of the group consisting of a fluid separation product, a gel electrophoresis product, and a liquid chromatography product;
    a length of the auxiliary structure is between 1 mm and 50 mm;
    a width of the auxiliary structure is between 20 μm and 200 μm;
    a depth of the auxiliary structure is between 8 μm and 30 μm.

6. The method of claim 1, wherein obtaining the position of the apparatus with respect to the fluidic flow path along a second direction on the surface based on the measure obtained comprises calculating the position using a mathematical function that defines a relationship between the measure and the position.

7. The method of claim 1, wherein including at least one auxiliary structure comprises forming the auxiliary structure using one of a lithography process and a laser treatment.

8. An apparatus for determining its position of with respect to a fluidic flow path on a surface of a fluidic product, the fluidic product further including at least one auxiliary structure, that is not a fluidic flow path, on the surface, the auxiliary structure having a known spatial relationship with the fluidic flow path, the apparatus comprising
    a detecting unit configured for obtaining a measure involving the auxiliary structure along a first direction on the surface;
    a determining unit configured for obtaining the position of the apparatus with respect to the fluidic flow path along a second direction on the surface based on the measure obtained with the detecting unit.

9. The apparatus of claim 8, wherein at least one of:
the first direction is different from the second direction;
the first direction is perpendicular to the second direction;
the auxiliary structure is a recess in the substrate;
the auxiliary structure is a color marking on or in the substrate;
the auxiliary structure is a bar on the substrate;
the auxiliary structure is a doped portion of the substrate;
the auxiliary structure is a mirror portion on or in the substrate;
the auxiliary structure is a metallic portion on or in the substrate;
the fluidic product comprises one of the group consisting of glass, a semiconductor, a plastic, a ceramic, and a metal;
the fluidic product comprises a fluid separation device, wherein the fluid separation device is one of the group consisting of a gel electrophoresis device, a pressure induced fluid separation device, and a liquid chromatography device;
the auxiliary structure is provided exclusively for determining the position of the apparatus with respect to the fluidic flow path;
the apparatus is configured as a fluidic product;
the apparatus is configured as a microfluidic product;
the apparatus is configured as a nanofluidic product;
the apparatus is configured as a microstructure product;
the apparatus is configured as a nanostructure product;
the apparatus is one of the group consisting of a fluid separation product, a gel electrophoresis product, and a liquid chromatography product;
a length of the auxiliary structure is between 1 mm and 50 mm;
a width of the auxiliary structure is between 20 μm and 200 μm;
a depth of the auxiliary structure is between 8 μm and 30 μm.

* * * * *